(12) United States Patent
Dirks

(10) Patent No.: US 6,938,867 B2
(45) Date of Patent: Sep. 6, 2005

(54) HOLDER FOR A POWERED DEVICE

(75) Inventor: Keith W. Dirks, Sterling, IL (US)

(73) Assignee: Wahl Clipper Corporation, Sterling, IL (US)

( * ) Notice: Subject to any disclaimer, the term of this patent is extended or adjusted under 35 U.S.C. 154(b) by 0 days.

(21) Appl. No.: 10/270,919

(22) Filed: Oct. 15, 2002

(65) Prior Publication Data

US 2004/0069920 A1 Apr. 15, 2004

(51) Int. Cl.⁷ .................................................. A47F 5/00
(52) U.S. Cl. ..................... 248/314; 248/309.1; 320/115
(58) Field of Search .......................... 248/316.7, 231.31, 248/231.81, 316.2, 316.5, 316.6, 309.1, 313, 311, 51, 52, 311.2; 439/151, 956, 259, 136; 320/111, 114, 115, 2; 30/43.92, 43.8, 41.6; 220/483

(56) References Cited

U.S. PATENT DOCUMENTS

| | | | | |
|---|---|---|---|---|
| 1,268,622 A | * | 6/1918 | Reynolds .................... 362/396 |
| 2,471,825 A | * | 5/1949 | Long .......................... 248/314 |
| 5,162,719 A | * | 11/1992 | Tomura et al. ............. 320/110 |
| 5,372,514 A | * | 12/1994 | Odemer et al. ............. 439/136 |
| 5,525,888 A | * | 6/1996 | Toya .......................... 320/111 |
| 6,065,728 A | * | 5/2000 | Spradlin .................... 248/309.1 |
| D427,564 S | * | 7/2000 | Wu ............................. D13/107 |
| 6,126,011 A | * | 10/2000 | Ullmann et al. ............ 206/576 |
| 6,417,645 B1 | * | 7/2002 | Yamaguchi et al. ........ 320/115 |
| 6,495,988 B1 | * | 12/2002 | Liao ........................... 320/111 |
| 2004/0209514 A1 | | 10/2004 | Yoe et al. ................... 439/529 |

FOREIGN PATENT DOCUMENTS

JP 4-354231 * 12/1992

* cited by examiner

Primary Examiner—Ramon O. Ramirez
Assistant Examiner—Tan Le
(74) Attorney, Agent, or Firm—Greer, Burns & Crain, Ltd.

(57) ABSTRACT

A holder for a powered device with a power supply, where the holder includes a cradle for seating the powered device, and a seating member for seating the power supply. The seating member and the cradle are preferably removably attached to each other at a pivot point. Preferably, the cradle and the seating member can be arranged together for holding the powered device in either a first or a second arrangement. In the first arrangement, the power supply is seated on the seating member and the cradle is attached to the seating member such that the power supply may be plugged into a wall outlet with the power supply and the powered device being fully supported against the wall by the holder. In the second arrangement, the power supply is not seated on said seating unit, but the seating unit is instead used as a base for the cradle.

16 Claims, 8 Drawing Sheets

HOLDER FOR A POWERED DEVICE

The present invention relates generally to a holder for a powered device, and more particularly to a holder that may be used to hold a powered device and its power supply (such as a transformer) against a wall, with the power supply plugged into an electrical outlet, as well as to a holder that may be reconfigured from a wall mounted holder to one that stands upon a countertop, as well as to a holder that includes a pivotable device cradle.

Currently, there are many different types of portable rechargeable powered devices that use a separate power supply (such as an AC transformer for either recharging a battery unit within the device or for powering the device directly when the AC transformer is plugged into both an electrical outlet and the powered device). Examples of such powered devices include hair clippers and trimmers; beard trimmers; electric toothbrushes; power drills, screwdrivers and other power tools; cellular telephones; PDAs and other handheld computers; etc.

Although there are currently many different holders available for powered devices with transformers (or other power units), most of the current holders suffer from a lack of versatility and/or they do not conveniently support the powered device and the transformer against a wall. For example, there are holders available that allow the user to plug the transformer into one electrical socket (of a two socket electrical outlet), which prevent access to the other electrical socket. Thus, there is a need for a holder that is versatile enough to be plugged into either the first or the second electrical socket (of a two docket outlet) without blocking access to the other socket, regardless of whether the sockets are arranged vertically or horizontally.

As another example, there are holders available that require mounting (via screws, adhesives, etc.) upon a wall, which are inconvenient due to the mounting time. In addition, such mountings may possibly damage the wall. Accordingly, it would be desirable to have a holder that can be more simply mounted to the wall.

Thus, the present invention provides a system for supporting a powered device, where that system includes a cradle that is configured and arranged to seat a powered device; and a seating member that is configured and arranged to seat a power supply that is associated with the powered device. When the transformer is plugged into an electrical outlet on a wall, and the power supply and the powered device are seated within the seating member and the cradle, respectively, the system for supporting is configured and arranged to fully support the cradle, the seating member, the powered device, the power supply, and a cord that connects the power supply to the powered device. Preferably, the system is fully supported against the wall without the need for screws, bolts, nails, adhesives, or similar attachment means, such that the user is only required to seat the power supply and the powered device upon the system, and plug the power supply into the electrical outlet.

The present invention also relates to a holder for a powered device with a power supply, where the holder includes a cradle that is configured and arranged to seat the powered device; and a seating member that is configured and arranged to seat the power supply that is associated with the powered device, wherein the seating member and the cradle are removably attached to each other at a pivot point. Such a pivotable arrangement makes the present invention versatile enough to be used for both vertically and horizontally oriented double socket electrical outlets without blocking the unused electrical socket, even when there is minimal space between the outlet and a corner or countertop.

The present invention also relates to a holder that includes a cradle that is configured and arranged to seat a powered device; and a seating member that is configured and arranged to seat a power supply that is associated with the powered device. Preferably, the cradle and the seating member may be arranged together for holding the powered device in either a first arrangement or a second arrangement. The first arrangement is an arrangement in which the power supply is seated on the seating member and the cradle is attached to the seating member such that the transformer may be plugged into a wall outlet with the power supply and the powered device being fully supported by the holder. The second arrangement is an arrangement in which the power supply is not seated on said seating unit, but the seating unit is instead used as a base for the cradle, thereby permitting the holder to be used as a freestanding unit for supporting the powered device.

BRIEF DESCRIPTION OF THE SEVERAL VIEWS OF THE DRAWINGS

Preferred embodiments of the present invention are described herein with reference to the drawings wherein.

DETAILED DESCRIPTION OF THE PREFERRED EMBODIMENTS

Figure 1:
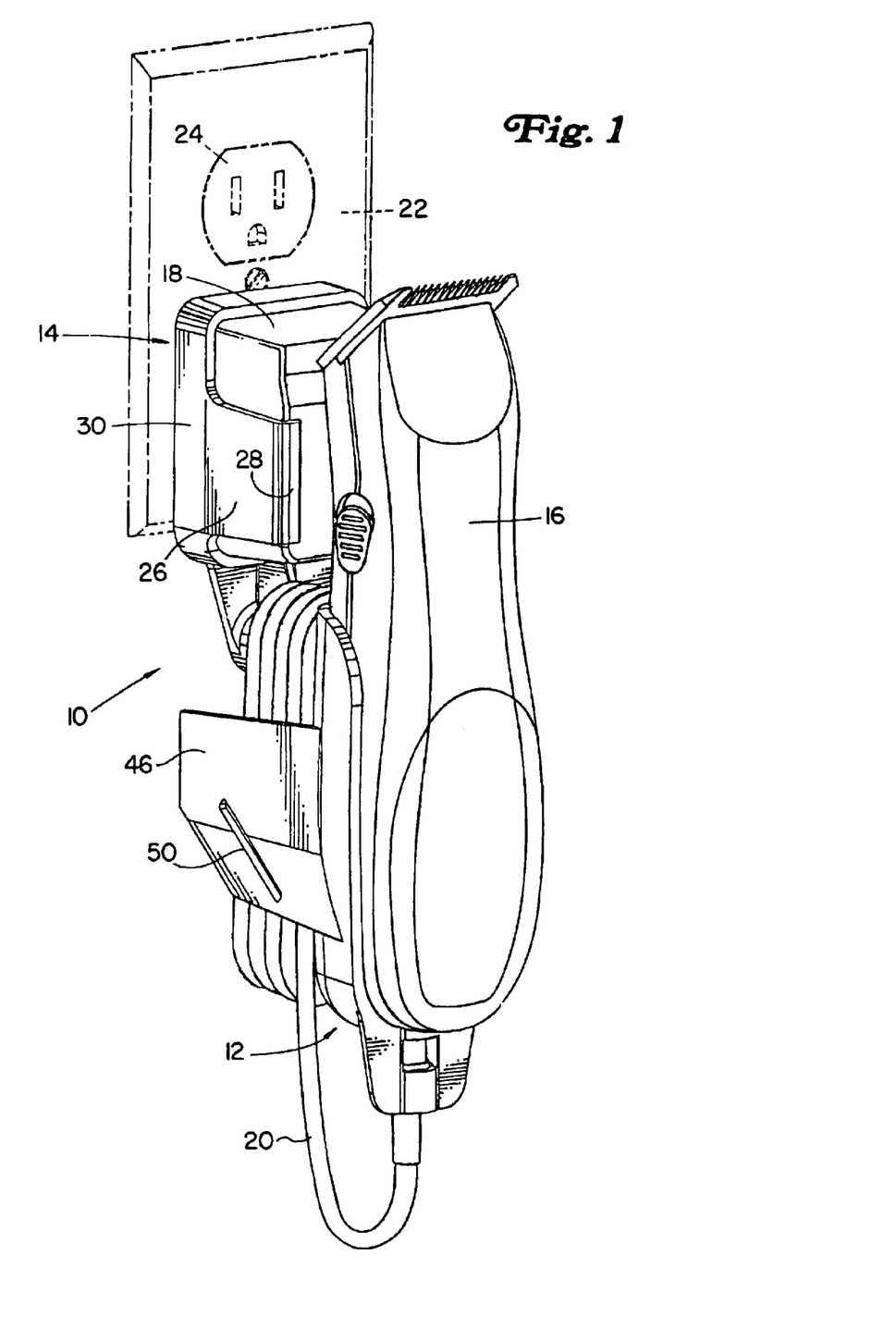
FIG. 1 shows a front perspective view of a first embodiment of the present invention, with the cradle pivoted so that its longitudinal axis coincides with the longitudinal axis of the power supply seating member.

Referring now to FIGS. 1–6, a first embodiment of the present invention will be described. FIG. 1 shows the holder 10, which, in this embodiment, is made from two separate components—a cradle 12 and a seating member 14. The cradle 12 is configured to seat a powered device, such as a hair trimmer 16, and the seating member 14 is configured to seat a power supply, such as transformer 18. Although in this example of the present invention a hair trimmer is being used as the powered device, the present invention may also be designed for use with other types of rechargeable devices (such as shavers, toothbrushes, cellular telephones, drills or other power tools, flashlights, etc.) that include a power supply to be plugged into an electrical outlet that is separate from the powered device. Further, the present invention may be used with devices that are intended to be stored upon the holder (such as a shaver or hair trimmer), as well as with devices that are only charged upon the holder (such as a cellular telephone, which is charged at night and taken with the user in the day). It is also contemplated that the present invention may be used with electrical devices that are not rechargeable, but that still include a separate power supply that is intended to be plugged into an electrical outlet, i.e., devices with the cord permanently attached. Further, the term "power supply," as used in this application, is intended to refer to a device for reducing a voltage and converting alternating current (AC) to direct current (DC), such as a transformer, as well as to devices that perform either of these functions, or other similar conversions, and to other types of power supplies, such as battery units.

One of the benefits of this embodiment of the present invention is that it enables the user to easily mount a powered device and its power supply against a wall by simply seating both components into the appropriate areas of the present holder 10 and plugging the device into the electrical outlet, without requiring the user to permanently attach the holder to the wall (via screws, adhesives, etc.). The FIG. 1 embodiment also fully supports the entire apparatus (powered device 16, transformer 18, and cord 20) against the wall, above the counter or other horizontal surface, thereby freeing up counter space and minimizing the risk that the cord (or another component) will be accidentally pulled, resulting in the powered device falling off of the counter.

Figure 2:
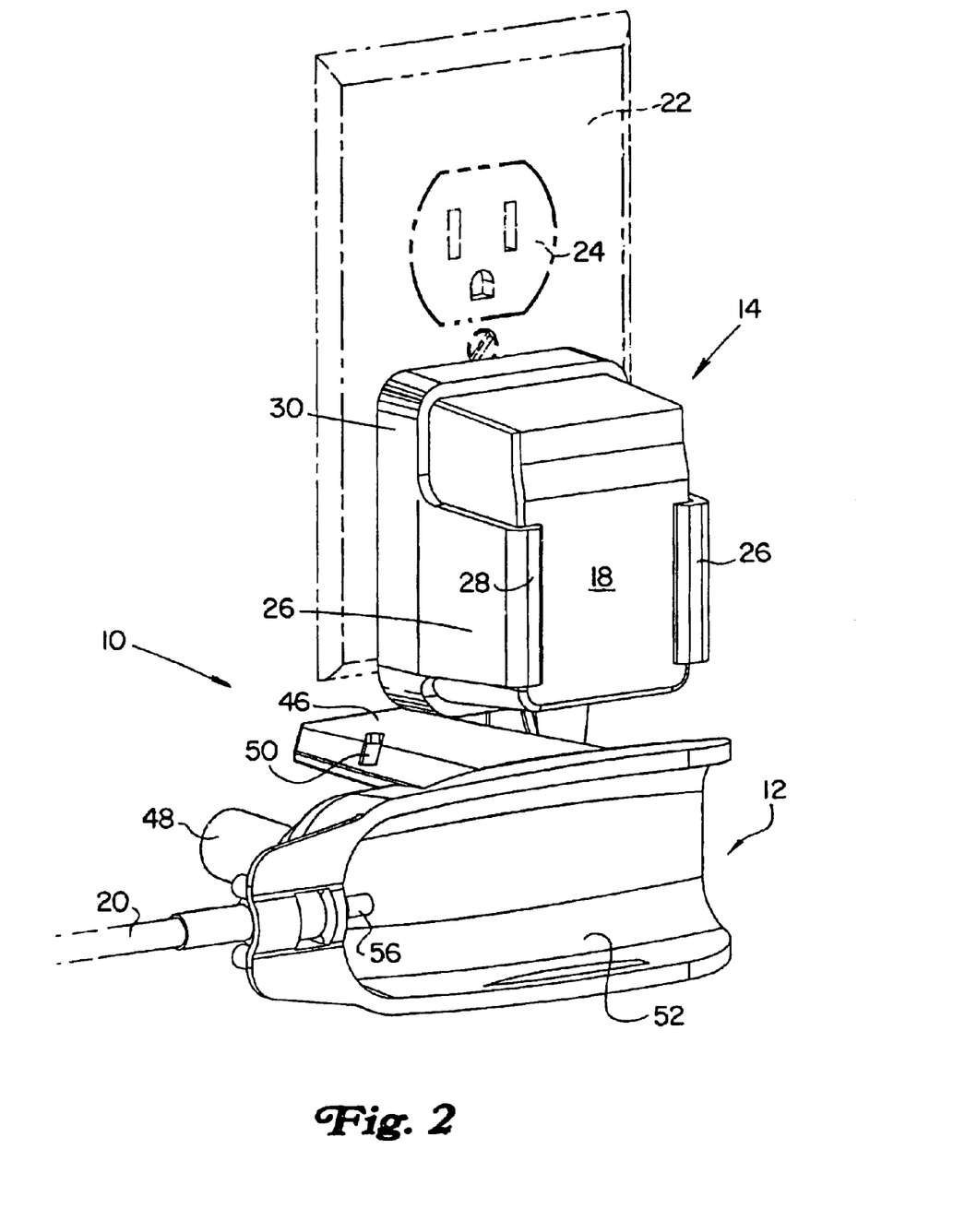
FIG. 2 shows the first embodiment with the cradle pivoted to be perpendicular to the power supply seating member.
Figure 3:
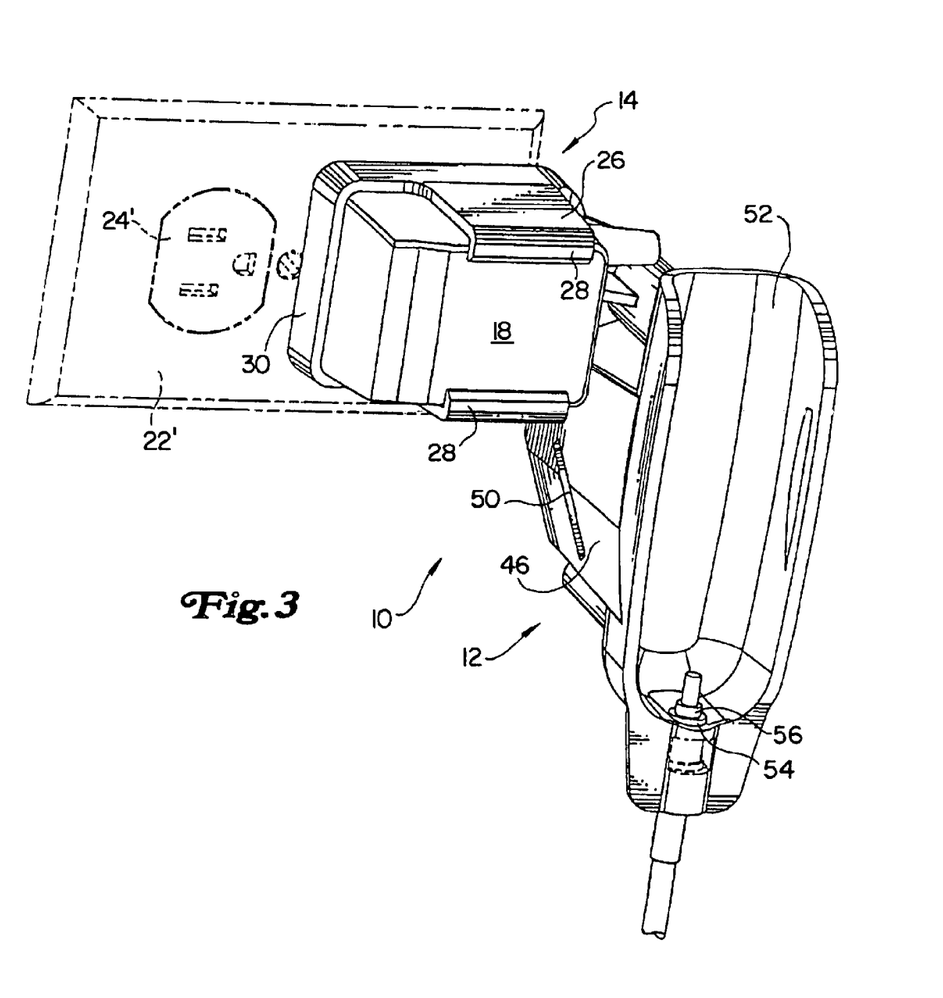
FIG. 3 shows the first embodiment, pivoted as in FIG. 2, except in this figure the transformer has been plugged into a horizontally extending outlet (as opposed to the vertically extending outlets of FIGS. 1 and 2)
Figure 4:
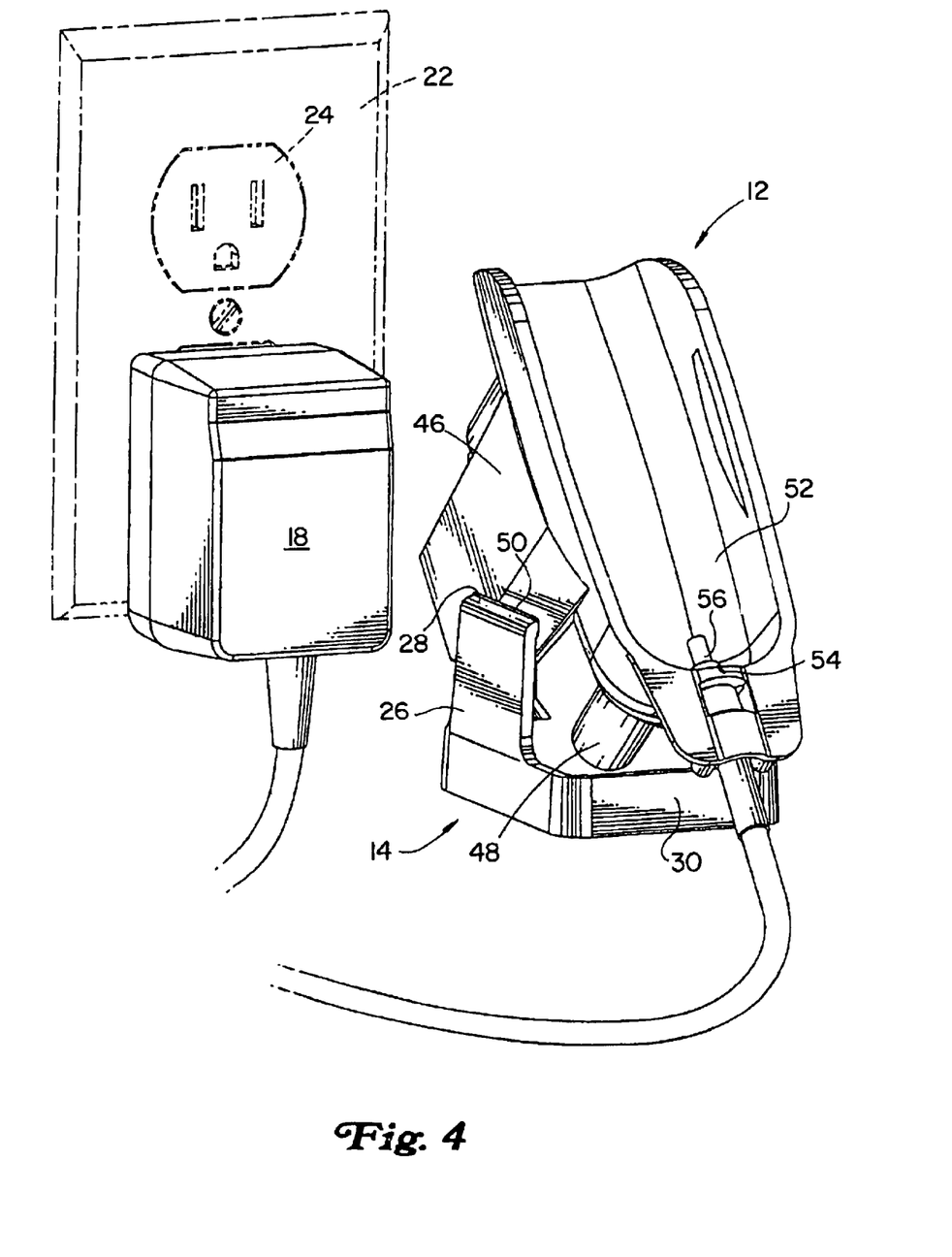
FIG. 4 shows the first embodiment, reconfigured so that the holder can be seated upon a horizontal surface such as a counter.

Another benefit of this embodiment of the present invention is that the holder 10 may be configured in several different ways, so that the transformer 18 can be plugged into one receptacle of an electrical outlet 22, without obstructing access to the second receptacle 24. FIG. 2 shows how the cradle 12 may be pivoted with respect to the seating member 14 if desired, such as when there is only a small amount of space available below the outlet 22. FIG. 3 shows how this first embodiment can also be used with a horizontally extending outlet 22', when the cradle 12 is pivoted in the same manner as that shown in FIG. 2. FIG. 3 also shows that the second receptacle 24' of this horizontal outlet 22' is still available for use, even when the transformer 18 is plugged into the first receptacle. Finally, FIG. 4 shows how the cradle 12 and the seating member 14 of the FIG. 1 embodiment can be repositioned to be used as a stand that can be positioned upon a counter top (as described more fully below).

Figures 5, 6:
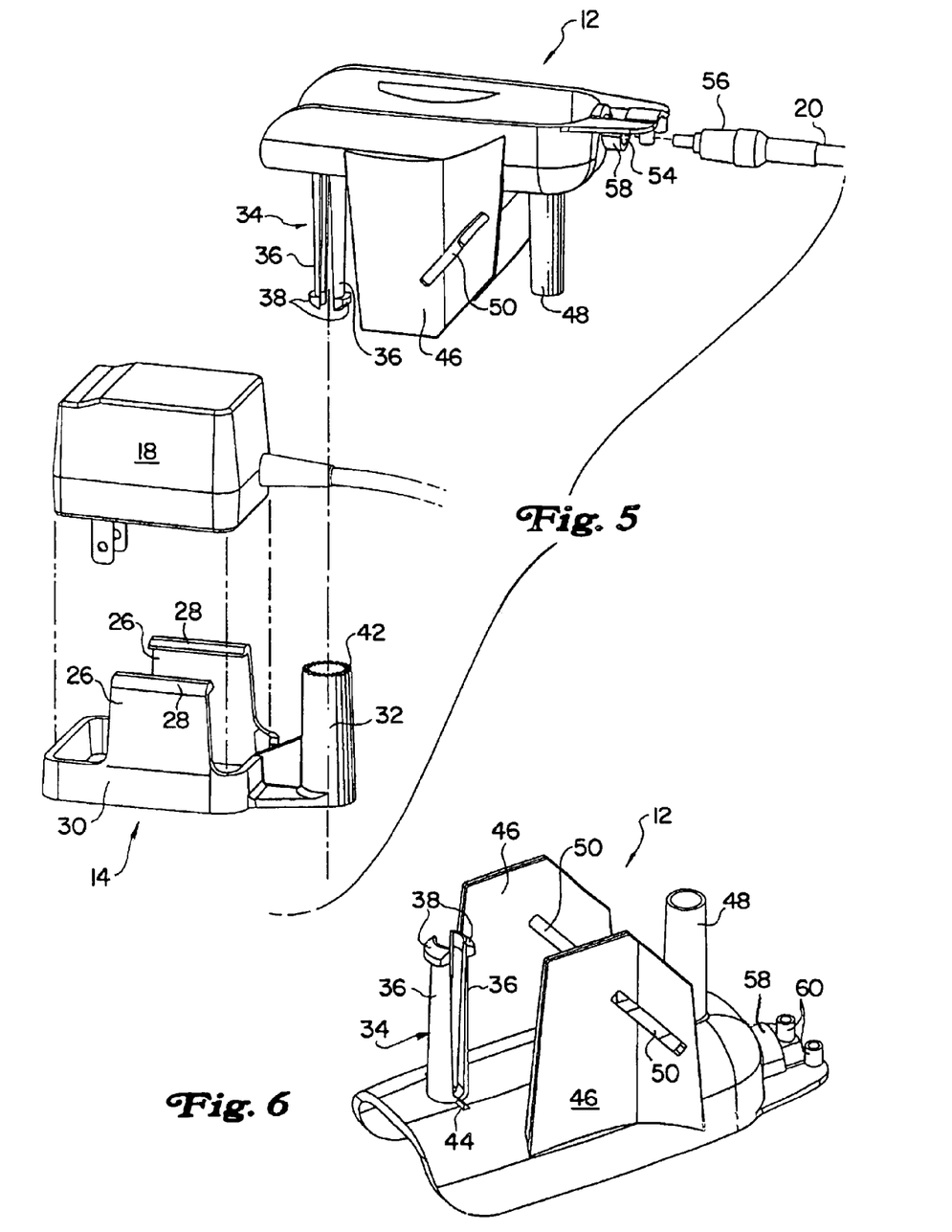
FIG. 5 shows an exploded view of the components of the first embodiment.
FIG. 6 shows the underside of the cradle of the first embodiment.

The structural details of the first embodiment of the present invention will now be described, while referring primarily to FIG. 5. The seating member 14 preferably includes two winged extensions 26 that each terminate in a bent lip portion 28. The winged extensions 26 preferably extend from a frame portion 30. As can be seen in FIG. 5, the frame portion 30 is open, which permits the plug of the transformer 18 to extend through the seating member 14, allowing the transformer 18 to be plugged into an electrical outlet. This combination of the frame 30, the wings 26 and the bent lip portions 28 is used to secure the transformer 18 to the seating member 14. It should be noted that the winged extensions 26 do not extend for the full height of the frame 30 (as shown in FIG. 1). Such a configuration facilitates insertion of the transformer 18 into the seating member 14. Although only one particular structure for securing the transformer has been shown and described, other means of securing the transformer to the holder are also contemplated as being within the scope of the invention.

Referring again to FIG. 5, this figure shows a hollow member 32 that extends outwardly from the bottom of the seating member 14. This hollow member 32 is part of an arrangement that allows for relative pivoting movement between the seating member 14 and the cradle 12. The hollow member is configured to accept the forked member 34 that extends from the underside of the cradle 12. As can be seen in FIG. 5, the forked member 34 includes two legs 36 that angle outwardly from each other as the forked member extends from the cradle 12. Moreover, each leg 36 preferably terminates in a bent tab 38.

In order to connect the cradle 12 to the seating member 14, the forked member 34 is inserted into the hollow member 32 until the bent tabs 38 extend through the hole 40 of the hollow member 32. Such an arrangement allows the cradle 12 and the seating member 14 to pivot with respect to each other, without separating from each other, because the bent tabs 38 hold the forked member 34 within the hollow member 32. When the user wants to separate the cradle 12 from the seating member 14, he simply applies a radially inwardly directed force to the legs 36, which allows the forked member 34 to be withdrawn from the hollow member 32.

The present invention also preferably includes a locking mechanism for locking the cradle 12, with respect to the seating member 14, into a single pivoted position, once a particular position has been selected from a plurality of available positions. The locking mechanism is preferably comprised of a plurality of ribs 42 that extend outwardly from one end of the hollow member 32 and a single rib 44 that extends from the underside of the cradle 12. In operation, the natural resilience of the outwardly extending legs 34 creates a relative bias against the end of the hollow member 32, which pushes the hollow member against the underside of the cradle 12, thereby pushing the plurality of ribs 42 into contact with the single rib 44, which prevents the cradle 12 from pivoting relative to the seating member 14, i.e., the cooperating ribs 42 and 44 lock the cradle into a single pivoted position. When the user wants to pivot the cradle 12 with respect to the seating member 14, the user lightly pulls the cradle 12 away from member 14 (easily overcoming the light bias created by forked member 34), which allows for the cradle to pivot. Upon releasing the cradle, the bias from the forked member 34 acts to mate rib 44 with ribs 42, thereby locking the cradle into the desired position. Of course, other pivot mechanisms are also contemplated as being within the scope of the invention.

With the locking mechanism of this embodiment, the cradle 12 may be locked into the position of FIG. 1 (with the longitudinal axis of the cradle 12 coinciding with the longitudinal axis of the seating member 14) or the position shown in FIG. 2 (with the longitudinal axis of the cradle 12 being perpendicular to the longitudinal axis of the seating member 14). In addition, the cradle may also be locked into a plurality of other positions, depending upon the rib configuration. However, if desired, the ribs may be configured to only permit locking into a limited number of positions (such as the positions of FIGS. 1 and 2, as well as the mirror image of FIG. 2 (i.e., with the cord 20 extending to the right)).

The remainder of the structural details of the cradle 12 will be described next, while primarily referring to FIGS. 5 and 6. The cradle 12 preferably includes two support ribs 46 that extend from the underside of the cradle 12. Although two support ribs 46 are shown and described, it is contemplated that more than two support ribs may be used, or even that a single support rib may be used. As shown in FIG. 1, when the transformer is plugged into an outlet 22, the support ribs 46 contact the wall (which is co-planer with the plate of the outlet 22), thereby helping to distribute the weight of the components against the wall. However, it is contemplated that if the wall terminates before reaching the area behind the support ribs, these ribs will simply hang freely, with the weight being fully supported by the seating member 14 and the plug of the transformer. Preferably, the support ribs 46 also provide an area behind which the cord 20 can be wrapped, which helps to maintain the cord partially out of sight, and suspended above the counter or other horizontal surface, as also shown in FIG. 1.

Referring back to FIGS. 5 and 6, the cradle 12 of this embodiment also preferably includes a post 48, which provides a surface upon which the cord may be wrapped (in combination with hollow member 32). In addition, the post 48 also provides support for the cradle 12 against the counter (or other horizontal surface) when the holder 10 is arranged as shown in FIG. 4.

Each of the support ribs 46 that extend from the underside of the cradle 12 also preferably include a slot 50, as shown in FIGS. 5 and 6. The slots 50 are configured to mate with the bent lips 28 of the seating members 14 when the holder 10 is arranged as shown in FIG. 4. The slots 50 are preferably provided at an angle so that the cradle 12 is seated in an inclined position when supported by the seating member 14 (as shown in FIG. 4). Such an incline provides for easy access to the powered device supported by the cradle 12, while still providing a stable seating area for the powered device.

The interior 52 of the front of the cradle 12 may be specially shaped to house a particular type of powered device (such as the interior 52 of the first embodiment is shaped to house a hair trimmer 16). In the alternative, it is also contemplated that the interior of the front of the cradle could also be shaped to house a variety of different powered devices, such as by providing some form of resilient arms or other securing means capable of seating items of a variety of different sizes and shapes.

The cradle 12 of the first embodiment also includes an aperture 54, which is configured and arranged to allow a portion of the cord 20 to pass therethrough. Preferably, the aperture 54 is sized to be an interference fit with the male connector 56 of the cord 20, whereby the male connector can be simply and securely seated in the aperture 54 of the cradle 12, while allowing the powered device (such as the hair trimmer 16) to be easily seated on the cradle for charging, as well as easily removed from the cradle for use (with the male connector 56 still attached to the cradle aperture 54). Such an interference fit also allows for easy removal of the male connector 56, such as when one desires to use the powered device with the cord attached (instead of using battery power from the rechargeable battery). In the alternative, the aperture 54 may be fitted with an adapter for transferring power between the male connector 56 and the powered device (such as hair trimmer 16). It is contemplated that different types of adapters could be provided with the holder so that a single holder can be used with a variety of different powered devices, where those different devices have a variety of different types of male connectors.

In addition, the cradle 12 may also optionally include a securing ring 58, as well as two (or more) pins 60, as shown in FIG. 6. The securing ring 58 and the pins 60 are used to provide additional support to maintain the male connector 56 (FIG. 5) in position when attached to the cradle 12.

Figure 7:
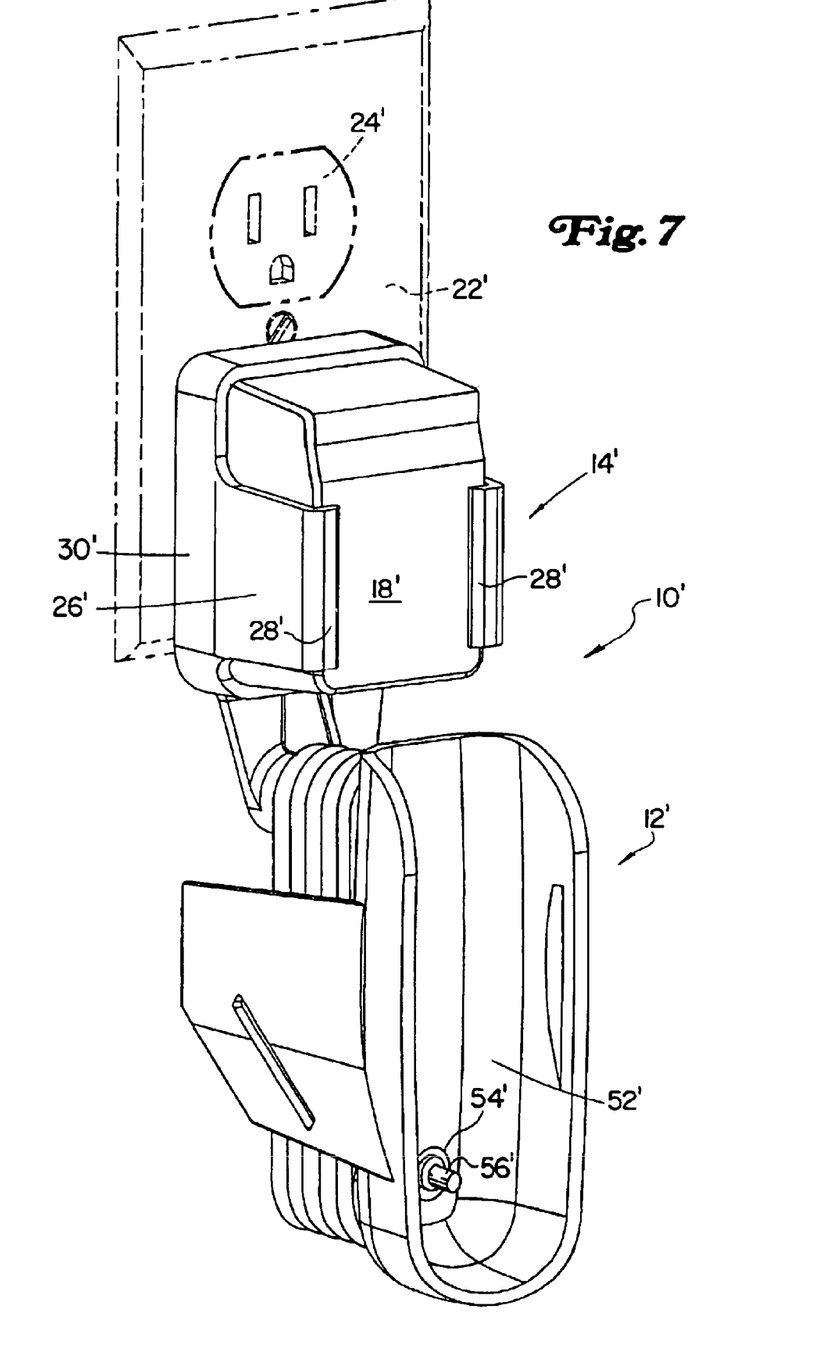
FIG. 7 shows a front perspective view of a second embodiment of the present invention, with the cradle pivoted so that its longitudinal axis coincides with the longitudinal axis of the power supply seating member.
Figure 8:
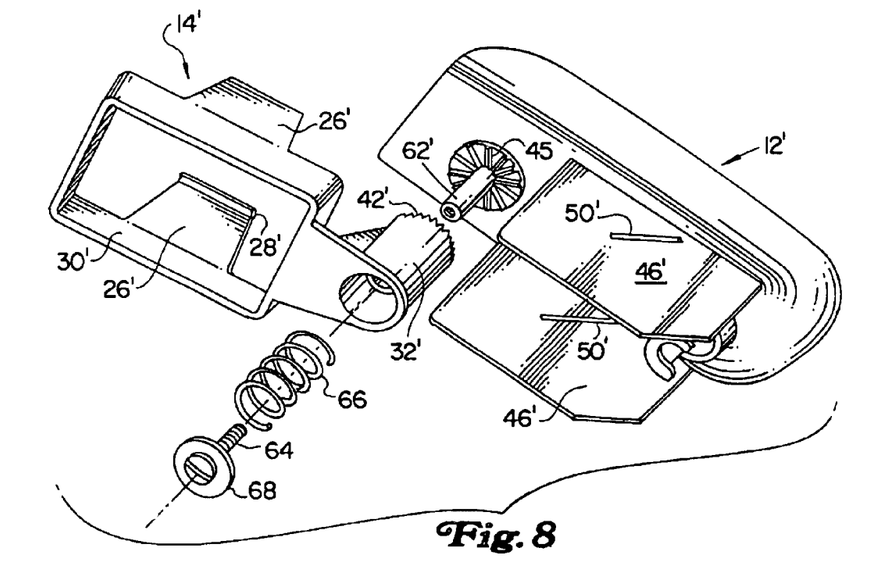
FIG. 8 shows an exploded view of the components of the second embodiment.

FIGS. 7 and 8 show a second embodiment (holder 10') of the present invention. In this embodiment, the features that are similar to those in the first embodiment of FIGS. 1–6 will be designated with the same reference numbers used earlier (except the prime designation will be added), and the descriptions of these features will be omitted. Only the features that are significantly different from the first embodiment will be described in detail.

The primary differences between the first embodiment and the second embodiment relate to the pivoting structure, the locking mechanism and the placement of the aperture for receiving the male connector of the cord. Referring now to FIG. 7, it can be seen that in this embodiment, the aperture 54' is located in the back of the cradle interior 52' (as opposed to the bottom of the cradle interior 52', as in the embodiment of FIGS. 1–6). Such placement of the aperture 54' allows for a cleaner look of the holder 10', such that less of the cord 20' and male connector 56' show when the powered device is seated upon the cradle 12'.

The second important difference between the first embodiment and this embodiment is the pivoting structure. As shown in FIG. 8, this embodiment includes an internally threaded shaft 62 that extends from the underside of the cradle 12' (components not found in the first embodiment, such as the internally threaded shaft 62, will be designated with new index numbers without a prime symbol). The threading of the internally threaded shaft 62 is configured to mate with the external threading of a screw 64 (or other type of externally threaded rod that includes an enlarged head). Also included in this embodiment is a spring 66 (or other biasing member). When assembled, the screw 64 is first inserted through the spring 66, and the screw 64 is then threaded into the internally threaded shaft 62. The spring is then contained within the hollow member 32', between the screw head 68 and an internal shoulder (not shown) that is located within the hollow member 32'. With this mechanism, the cradle 12' and the seating member 14' are biased together. When pivoting is desired, the user simply apples a force to slightly separate the cradle 12' from the seating member 14'. When the desired location is found, the force is removed, which allows the members to be biased into a locked position.

In this embodiment, as in the first embodiment, the cradle 12' and the seating member 14' may be locked into a particular pivoted position with respect to each other via mating ribs, as described above when describing the first embodiment. In the alternative, instead of using a single rib 44 (as shown in FIG. 5 of the first embodiment), the locking mechanism of this embodiment may employ multiple ribs 45, which lock against the multiple ribs 42'.

When the user desires this second embodiment to be arranged to sit upon a horizontal surface, the screw 64 and spring 66 are removed, and the cradle 12' is seated upon the seating member 14' in a manner resembling the FIG. 14 view of the first embodiment.

Figure 9:
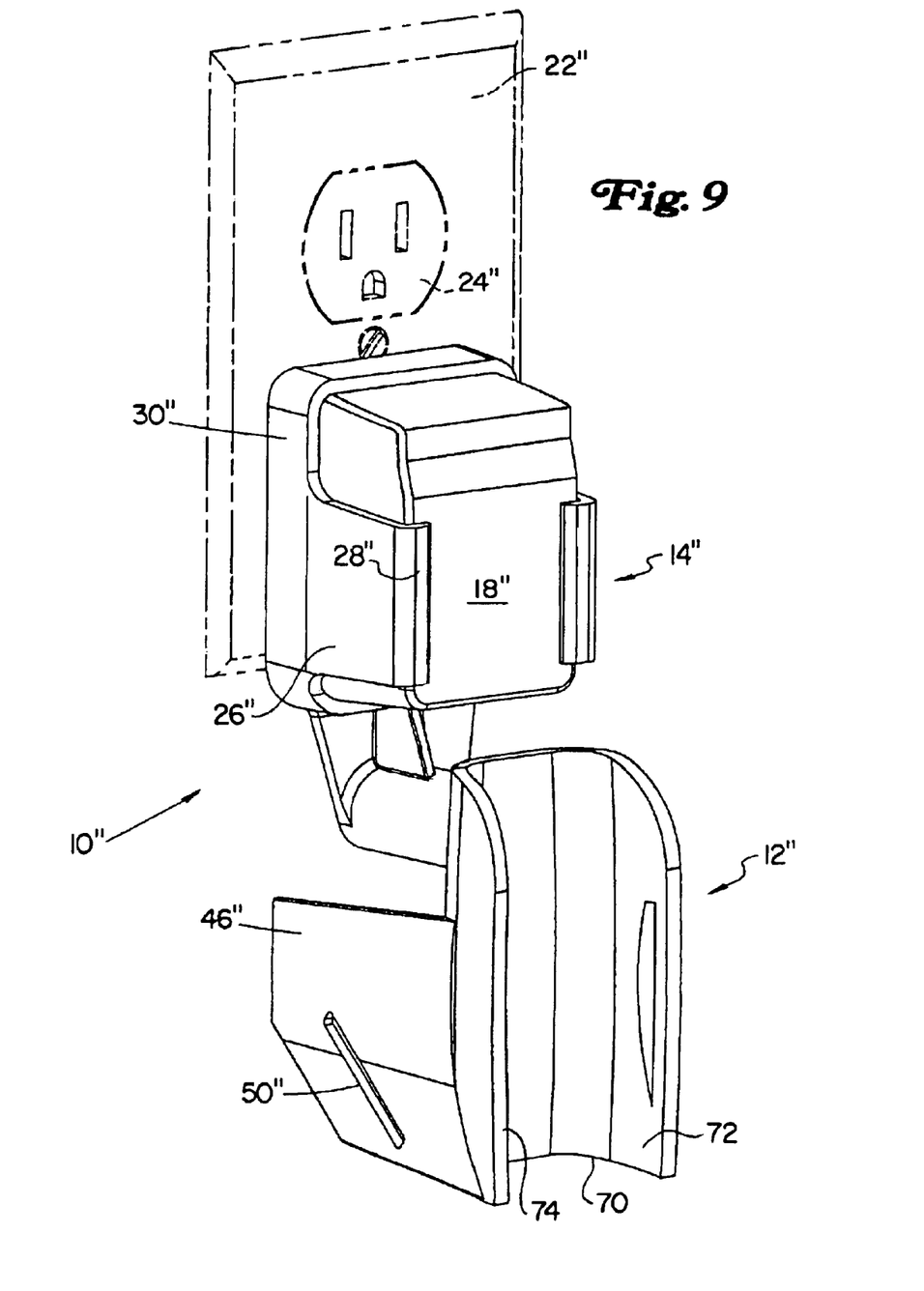
FIG. 9 shows a front perspective view of a third embodiment of the present invention, with the cradle pivoted so that its longitudinal axis coincides with the longitudinal axis of the power supply seating member.

FIG. 9 depicts a third embodiment of the present invention. In this embodiment, index numbers with a double prime symbol will be used to refer to components that are similar to those components of the earlier embodiments, and new index numbers without any prime symbols will be used to refer to features that have not been described in the previously-discussed embodiments.

The primary difference between this embodiment and the earlier embodiments is that this embodiment lacks an aperture (such as aperture 54 of FIGS. 5 and 6 or aperture 54' of FIG. 7). Instead, in this embodiment, the lower portion 70 of the cradle 12" has been truncated. Such a truncated lower portion 70 allows the cradle 12" to accept powered devices of a wide variety of different lengths with a wide variety of differently-shaped lower portions. This is the case because the lower portion 70 of the cradle is open, and therefore the shape of the lower portion of the powered device does not restrict its ability to be seated within the cradle. However, one drawback of this embodiment is that since it lacks an aperture for holding the male connector of the cord, this component is not neatly seated upon the holder. Thus, this embodiment is preferred when a more universal holder is desired, or for cases where the powered device will normally be used with the cord attached (such as in those devices without rechargeable batteries located within the powered unit).

While various embodiments of the present invention have been shown and described, it should be understood that other modifications, substitutions and alternatives may be apparent to one of ordinary skill in the art. Such modifications, substitutions and alternatives can be made without departing from the spirit and scope of the invention, which should be determined from the appended claims. It should also be noted that features of one embodiment may be incorporated into the other embodiments.

Various features of the invention are set forth in the appended claims.

What is claimed is:

1. A system for supporting a powered device having a power supply, comprising:
   a cradle that is configured and arranged to seat the powered device; and
   a seating member that is configured and arranged to seat the power supply;
   wherein when the power supply and the powered device are adapted to be seen seated within said seating member and said cradle, respectively, the system for supporting is configured and arranged to fully support said cradle, said seating member, the powered device, and the power supply;
   further wherein:
   said seating member includes two winged extensions that are configured and arranged to removably secure the power supply to said seating member; and
   said cradle includes a first support rib and a second support rib, wherein both of said support ribs are configured and arranged to contact a wall when said system is in an arrangement with the powered device seated on said cradle, the power supply seated on said seating member, and a plug of said power supply inserted into an outlet in the wall.

2. The system as defined in claim 1, wherein:
   said winged extensions of said seating member each terminate in a bent lip portion; and
   said first and second support ribs of said cradle each include a slot, wherein said slots of said first and second support ribs and said bent lips of said winged extensions are configured and arranged to mate with each other so that said cradle can be attached upon said seating member when the power supply is not seated within said seating member.

3. A holder for a powered device with a power supply, said holder comprising:
   a cradle that is configured and arranged to hold the powered device; and
   a seating member that is configured and arranged to hold the power supply that is associated with the powered device, wherein said seating member and said cradle are removably attached to each other at a pivot point, further including a locking mechanism for locking said cradle, with respect to said seating member, into a single pivoted position selected from a plurality of available pivoted positions.

4. The holder as defined in claim 3, wherein said cradle first can be pivoted at least 90 degrees about said pivot point between a first position and a second position.

5. The holder as defined in claim 4, wherein said first position of said cradle is a position in which a longitudinal axis of said cradle coincides with a longitudinal axis of said seating member, and said second position of said cradle is a position is which said longitudinal axis of said cradle is perpendicular to said longitudinal axis of said seating member.

6. The holder as defined in claim 3, wherein said locking mechanism includes a single first rib located on a portion of one of said cradle or said seating member and a plurality of second ribs that are configured and arranged to mate with said first rib and that are located on a portion of the other of said cradle and said seating member, wherein said plurality of second ribs are biased towards said first rib such that said cradle can be locked into a single pivoted position with respect to said seating member.

7. The holder as defined in claim 3, wherein said locking mechanism includes two sets of mating ribs, with a first set being located on a portion of said cradle and a second set being located on a portion of said seating member, wherein at least one of said two sets of locking ribs are biased against the other set of locking ribs for locking said cradle into a single pivoted position with respect to said seating member.

8. The holder as defined in claim 3, further comprising:
   a forked member extending from one of said cradle or said seating member; and
   a hollow member extending from the other of said cradle and said seating member, wherein said hollow member is configured and arranged to mate with said forked member to define said pivot point.

9. The holder as defined in claim 8, wherein said forked member includes two legs that angle outwardly from each other when viewed from proximal ends to distal ends, with each of said legs including a tab formed on said distal end thereof, such that when said forked member is located within said hollow member, said angled legs bias said cradle and said seating member against each other and said tabs keep said cradle and said seating member from separating from each other, unless a force is applied to push said legs together.

10. The holder as defined in claim 3, further comprising:
    an internally threaded shaft extending from a portion of said cradle;
    a hollow member extending from a portion of said seating member, and including a first end and a second end, said hollow member also including an internal shoulder between said first and second ends;
    a biasing member positioned within said hollow member, between said first end and said internal shoulder; and
    a threaded rod, said threaded rod being configured to extend through said biasing member, through a portion of said hollow member, and into said internal threading of said internally threaded shaft, such that said biasing member exerts a force upon said internal shoulder to bias said seating member against said cradle member.

11. A holder for a powered device with a power supply, said holder comprising:
    a cradle that is configured and arranged to hold the powered device; and a seating member that is configured and arranged to hold the power supply that is associated with the powered device, wherein said seating member and said cradle are removably attached to each other at a pivot point, wherein said cradle includes an aperture therein, where said aperture is configured and arranged to allow a portion of a cord to pass therethrough.

12. The holder as defined in claim 3, further comprising:

at least one support rib extending from said cradle, said support rib being configured and arranged to contact a wall which includes an outlet into which a plug of said power supply may be inserted; and at least two winged extensions extending from said seating member, said winged extensions being configured and arranged to removably secure the power supply to said seating member.

13. A holder comprising:

a cradle that is configured and arranged to seat a powered device; and a seating member that is configured and arranged to seat a power supply that is associated with the powered device;

wherein said cradle and said seating member may be arranged together for holding the powered device in either a first arrangement or a second arrangement, where:

said first arrangement is an arrangement in which the power supply is adapted to be seated on said seating member and said cradle is attached to said seating member such that the power supply may be plugged into a wall outlet with the power supply and the powered device being fully supported by said holder; and said second arrangement is an arrangement in which the power supply is not seated on said seating unit, but the seating unit is instead used as a base for said cradle, thereby permitting said holder to be used as a free-standing unit for supporting said powered device, and further including at least one support rib extending from said cradle, said a least one support rib being configured and arranged to contact a wall that includes the electrical outlet, such that at least a portion of the combined weight of said cradle, said seating member, the power supply, and the powered device is supported by said at last one support rib, when said holder is in use with the power supply being plugged into the wall outlet.

14. The holder as defined in claim 13, wherein said cradle includes an aperture therein, where said aperture is configured and arranged to allow a portion of a cord to pass therethrough.

15. The holder as defined in claim 13, further comprising:

two support ribs extending from said cradle, each of said support ribs including a slot; and two winged extensions extending from said seating member, said winged extensions being used to secure the power supply to said seating member when said holder is arranged into said first arrangement, but when said holder is arranged into said second arrangement, said winged extensions are inserted into said slots on said support ribs.

16. The holder as defined in claim 13, wherein when said holder is arranged into said first arrangement, said seating member and said cradle are attached to each other at a pivot point, such that said cradle can be rotated at least 90 degrees on said pivot point.

* * * * *

UNITED STATES PATENT AND TRADEMARK OFFICE
CERTIFICATE OF CORRECTION

PATENT NO. : 6,938,867 B2
DATED : September 6, 2005
INVENTOR(S) : Keith W. Dirks

It is certified that error appears in the above-identified patent and that said Letters Patent is hereby corrected as shown below:

Column 7,
Line 26, delete "seen".

Column 10,
Line 7, delete "a least" and insert -- at least --.

Signed and Sealed this

Eleventh Day of April, 2006

JON W. DUDAS
*Director of the United States Patent and Trademark Office*